United States Patent [19]

Krepski et al.

[11] Patent Number: 4,918,231

[45] Date of Patent: Apr. 17, 1990

[54] PROCESS FOR THE PRODUCTION OF 1,2-AMINO ALCOHOLS

[75] Inventors: Larry R. Krepski; Steven M. Heilmann; Jerald K. Rasmussen, all of St. Paul, Minn.

[73] Assignee: Minnesota Mining and Manufacturing Company, St. Paul, Minn.

[21] Appl. No.: 284,595

[22] Filed: Dec. 15, 1988

Related U.S. Application Data

[63] Continuation of Ser. No. 635,452, Jul. 30, 1984, abandoned.

[51] Int. Cl.$^4$ .................. C07C 91/23; C07C 91/14; C07C 85/12
[52] U.S. Cl. .................. 564/363; 564/462; 564/493; 564/364
[58] Field of Search .................. 564/363, 462, 493

[56] References Cited

U.S. PATENT DOCUMENTS 4,119,710  10/1978  Engelhardt et al. .................. 424/282

OTHER PUBLICATIONS

D. Lednicer and L. A. Mitscher, "The Organic Chemistry of Drug Synthesis", John Wiley and Sons, New York, 1977, pp. 62–84.
J. A. Frump, Chem. Rev., 71, 483 (1971).
I. Okada, K. Ichimura, R. Sudo, Bull. Chem. Soc. (Japan), 43, 1185 (1970).
I. Elphimoff-Felkin, Bull. Soc. Chem. FR., 784 (1955).
J. K. Rasmussen and S. M. Heilmann, Synthesis, (1978), pp. 219–222.
Tetrahedron Letters, vol. 24, No. 38, 1983, pp. 4075–4078, London, GB; L. R. Krepski et al.: "Addition of Grignard Reagents to O-Trimethylsilylated Cyanohydrins: Synthesis of Acyloins".
Journal of the Chemical Society, Chemical Communications, No. 1, 1973, pp. 55–56, London, GB: D. A. Evans et al.: "Cyanosilylation of Aldehydes and Ketones, a Convenient Route to Cyanohydrin Derivatives".
Comptes Rendus Hebdomadaires des Seances de L'Academie des Sciences, vol. 236, Jan.-Jun. 1953, pp. 387–389, Paris, FR; I. Elphimoff-Felkin et al.: "Synthese d'Kappa-Ceto et Kappa-Amino-Alcools a Partir de Cyanhydrines, I. Cyanhydrine de la Cyclohexanone".
Bulletin de la Societe Chimique de France, No. 140, 1955, pp. 784–789, Paris, FR; I. Elphimoff-Felkin "Sur une Nouvelle Methode Generale de Synthese des Kappa-Cetols et Kappa-Amino-Alcools a Fonction Alcool Tertiaire".
Chemical Abstracts, vol. 95, No. 7, Aug. 17, 1981, p. 662, col. 1, Abstract No. 61556u, Columbus, Ohio, U.S.; R. Amouroux et al.: "A New Synthesis of Beta-Amino Alcohols via O-Silylated Cyanohydrins", & Synthesis 1981, (4), 270–272.
European Search Report.
*The Chemistry of the Cyano Group*, Z. Rappoport, ed., Interscience Publishing (London: 1970), pp. 276–280.
Allen et al., *J. Amer. Chem. Soc.*, 61, 1790–1794 (1939).
S. Kuwada and Y. Sasagawa, *Bull. Chem. Soc. Japan*, 16, 423–427 (1941).
Gould, *Mechanism and Structure in Organic Chemistry*, Holt, Rinehard and Winston (New York: 1959), pp. 400–401.

Primary Examiner—Richard L. Raymond
Assistant Examiner—Susan P. Tranor
Attorney, Agent, or Firm—Donald M. Sell; Walter N. Kirn; David L. Weinstein

[57] ABSTRACT

A process for the production of 1,2-amino alcohols, in improved yields, comprising the steps of:
(1) reacting a silylated cyanohydrin compound with a Grignard reagent;
(2) treating the reaction product of Step 1 with either a reducing agent, or an organolithium compound;
(3) hydrolyzing the reaction product of Step 2;
(4) isolating the resulting 1,2-amino alcohol.

The 1,2-amino alcohols thus formed are useful as pharmaceuticals or precursors therefor.

17 Claims, No Drawings

PROCESS FOR THE PRODUCTION OF 1,2-AMINO ALCOHOLS

This is a continuation of application Ser. No. 635,452 filed July 30, 1984, now abandoned.

BACKGROUND OF THE INVENTION

1. Field of the Invention

This invention relates to a process for preparing 1,2-amino alcohols.

2. Description of the Background Art 1,2-Amino alcohols (sometimes called beta-aminoalcohols) are compounds with an amino group and a hydroxyl group on adjacent carbon atoms. They are of considerable commercial importance, particularly in the pharmaceutical industry. Many 1,2-amino alcohols are important as drugs or as intermediates for the preparation of drugs (D. Lednicer and L. A. Mitscher, "The Organic Chemistry of Drug Synthesis", John Wiley and Sons, New York, 1977, pp. 62–84). Additionally, 1,2-amino alcohols are useful intermediates for the preparation of various heterocycles such as oxazolines (J. A. Frump, *Chem. Rev.*, 71, 483 (1971)) or aziridines (I. Okado, K. Ichimura, R. Sudo, *Bull. Chem. Soc.* (Japan), 43, 1185 (1970)).

Of the several methods which have been developed for the preparation of 1,2-amino alcohols, few are general, versatile, provide high yields, or employ readily available starting materials.

A method for the synthesis of 1,2-amino alcohols which is similar to the process of the present invention has been reported in I. Elphimoff-Felkin, *Bull. Soc. Chem. Fr.*, 784 (1955). In this method, the tetrahydropyranyl ether of a cyanohydrin,

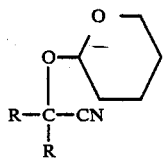

was reacted with a Grignard reagent, R'MgX, and then the intermediate product was reduced with lithium aluminum hydride ($LiAlH_4$). One shortcoming of this method is the necessity of first converting a ketone to its cyanohydrin, then converting this cyanohydrin to its tetrahydropyranyl ether. Both steps occur with varying degrees of efficiency, and yields are not uniformly high. A second shortcoming is that the reaction was not demonstrated to be general, i.e. applicable with essentially any ketone, since the only examples reported were with acetone, cyclopentanone, and cyclohexanone. The third shortcoming is that the only reducing agent which was demonstrated to be effective for reduction of the intermediate product was lithium aluminum hydride, $LiAlH_4$, and its use provided only poor to moderate yield of product. In addition, lithium aluminum hydride is a hazardous reagent.

SUMMARY OF THE INVENTION

The present invention involves a process for producing 1,2-amino alcohols. The process comprises the steps of:

(1) reacting a silylated cyanohydrin compound with a Grignard reagent;

(2) treating the reaction product of Step 1 with either a reducing agent or an organolithium compound, (3) hydrolyzing the reaction product of Step 2; and (4) isolating the resulting 1,2-amino alcohol.

The method of the present invention results in formation of 1,2-amino alcohols in high overall yield and, generally, with fewer steps than with previously known synthetic methods. In addition, the present method is more general, being applicable with essentially any aldehyde or ketone starting material. Furthermore, with the method of this invention, the reduction of the intermediate reaction product can be accomplished with a variety of different reducing agents and is not limited to the use of lithium aluminum hydride. The process of this invention can also be used to prepare various mixtures of the 1,2-amino alcohol diastereomers. The versatility of being able to use different reducing agents or reducing step conditions or both in the present invention results in the production of diastereomeric products with the two stereoisomers in different ratios, an important feature because the individual diastereomers of a 1,2-amino alcohol often have very different physical and biological properties.

DETAILED DESCRIPTION OF THE INVENTION

Silylated cyanohydrins that are preferred for use in the process of this invention can be represented by the formula:

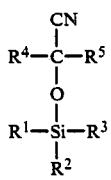

wherein $R^1$, $R^2$, and $R^3$ can be the same or different and independently represent a member of the group consisting of hydrogen, alkyl groups, e.g., containing 1 to 6 carbon atoms, aralkyl groups, e.g. containing 7 to 12 carbon atoms, alkaryl groups, e.g. containing 7 to 12 carbon atoms, aryl groups, e.g., containing 6 to 14 carbon atoms, alkoxy groups, e.g., containing 1 to 6 carbon atoms, and $R^4$ and $R^5$ independently represent a member of the group consisting of hydrogen, alkyl groups, e.g. containing 1 to 30 carbon atoms, aralkyl groups, e.g., containing 7 to 30 carbon atoms, alkaryl groups, e.g., containing 7 to 30 carbon atoms, aryl groups, e.g., containing 6 to 30 carbon atoms, or $R^4$ and $R^5$, along with the carbon atom to which they are bonded, together represent a cycloalkyl group, e.g., containing 3 to 30 carbon atoms, said alkyl, cycloalkyl, aralkyl, alkaryl, and aryl groups of $R^1$, $R^2$, $R^3$, $R^4$, and $R^5$ being optionally substituted with various groups which are inert to the reaction conditions of step (1), e.g., alkoxy, aryloxy, alkaryloxy, aralkoxy, silyloxy, and halo.

Silylated cyanohydrin compounds useful in this invention are well-known in the art and can be prepared by reacting an aldehyde or ketone with a silyl cyanide, optionally in the presence of a catalyst. The reaction between the silyl cyanide and the aldehyde or ketone can take place in the absence or presence of solvent. Examples of solvents useful for the reaction are polar aprotic solvents, such as acetonitrile, N,N-dimethylformamide, N,N-dimethylacetamide and N-methylpyrrolidone, or non-polar aprotic solvents such as benzene, toluene, chloroform, methylene chloride, hexane, pentane, and mixtures thereof. Solvents that are unsuitable for the reaction are those which would react with the silyl cyanide reactant or the silylated cyanohydrin product. These include water and alcoholic solvents. The reaction may be conducted in the presence of catalysts, such as zinc cyanide and zinc iodine, to hasten formation of the silylated cyanohydrin product.

Choice of the $R^1$, $R^2$, and $R^3$ groups is not particularly important since those groups are not retained in the final product. Preferred $R^1$, $R^2$, and $R^3$ groups are methyl, because the trimethylsilyl cyanide reagent is commercially available or can be formed in situ as described below.

Although the trimethylsilyl cyanide reagent used in this invention is commercially available, methods are known for generating the trimethylsilyl cyanide reagent in situ. J. K. Rasmussen and S. M. Heilmann (*Synthesis*, (1978), pp. 219-221) describe a method for synthesizing silylated cyanohydrins which involves reacting an aldehyde or ketone with chlorotrimethylsilane and potassium cyanide in a solvent such as acetonitrile or N,N-dimethylformamide. The reaction is accomplished by adding the carbonyl compound (0.1 mol) to a stirred suspension of potassium cyanide (0.3 mol) in solvent (20 ml), trimethylsilyl chloride (0.16 mol) and, optionally, zinc iodide (0.05 g). The mixture is refluxed gently and monitored by gas-liquid chromatography. On completion, the reaction mixture is filtered, the filter cake washed with dry solvent and filtered, and the combined filtrates concentrated in vacuo. Distillation at reduced pressure affords pure silylated cyanohydrins.

Representative examples of silylated cyanohydrins that are suitable for use in the process of this invention are the silylated cyanohydrins of cyclohexanecarboxaldehyde, butyraldehyde, benzaldehyde, p-anisaldehyde, p-tolualdehyde, m-dimethylaminobenzaldehyde, o-chlorobenzaldehyde, phenylacetaldehyde, pivaldehyde, pyridine-2-carboxaldehyde, p-nitrobenzaldehyde, cinnamaldehyde, crotonaldehyde, 7-methoxy-3,7-dimethyloctanal, phenylpropargylaldehyde, 9-anthraldehyde, 3-benzyloxy-4-methoxybenzaldehyde, 4-biphenylcarboxaldehyde, 2-fluorenecarboxaldehyde, p-fluorobenzaldehyde, 4-trimethylsilyloxybenzaldehyde, 2-naphthaldehyde, 1-pyrenecarboxaldehyde, ferrocenecarboxaldehyde, 2-furaldehyde, 5-methyl-2-thiophenecarboxaldehyde, l-perillaldehyde, 1,2,3,6-tetrahydrobenzaldehyde, acetylacetaldehyde dimethylacetal, 5-trimethylsilyloxy-2-pentanone, 5-chloro-2-pentanone, 4-dodecyloxybenzophenone, 9-heptadecanone, mesityl oxide, 3-methylthio-2-butanone, 10-nonadecanone, 2-adamantanone, dibenzosuberone, 4-chromanone, acetone, methyl ethyl ketone, cyclohexanone, camphor, acetophenone, benzophenone, deoxybenzoin, fluorenone, cyclododecanone, 3-cholestanone, and γ-chloro-p-fluorobutyrophenone.

Grignard reagents that are preferred for use in the process of this invention can be represented by the formula:

$$R^6MgX \qquad \text{II}$$

wherein
$R^6$ represents a member selected from the group consisting of alkyl groups, e.g., containing 1 to 30 carbon atoms, aralkyl groups, e.g., containing 7 to 30 carbon atoms, alkaryl groups, e.g., containing 7 to 30 carbon atoms, and aryl groups, e.g., containing 6 to 30 carbon atoms, said groups being optionally substituted with various groups which are inert to the reaction conditions of step (1), such as alkoxy, aryloxy, alkaryloxy, aralkoxy, silyloxy, and halo, and X represents chloro, bromo or iodo.

Preparation of the Grignard reagent is well-known in the art and is discussed in detail in M. S. Kharasch and O. Reinmuth, *Grignard Reactions of Nonmetallic Substances*, Prentice-Hall, Englewood Cliffs, N.J. (1954), Chapter 2. In general, an organohalogen compound is allowed to react with magnesium in an anhydrous solvent to yield the organomagnesium halide, i.e., the Grignard reagent. Useful solvents for preparing Grignard reagents include benzene, toluene, diethyl ether, tetrahydrofuran, diisopropyl ether, and methyl t-butyl ether, with the ether solvents being preferred. The process for forming the Grignard reagent is generally exothermic; consequently, the organohalogen compound is generally dissolved in the solvent and added portionwise or dropwise to the magnesium metal immersed in the same solvent such that mild refluxing of the solvent occurs, thus moderating the exothermicity of the reaction. The mixture can be heated for about 1 to 2 hours to ensure complete reaction of all the added organohalogen compound. The reaction mixture should then be allowed to cool to room temperature (about 25° C.) whereupon it can then be used directly in the process of the invention.

Representative examples of Grignard reagents that are suitable for use in the process of this invention are methylmagnesium chloride, ethylmagnesium iodide, ethylmagnesium bromide, n-propylmagnesium chloride, n-butylmagnesium chloride, n-hexylmagnesium bromide, tetramethylenedimagnesium dibromide, n-octylmagnesium chloride, phenylmagnesium bromide, p-chlorophenylmagnesium bromide, phenylmagnesium chloride, 9-phenanthrylmagnesium bromide, cinnamylmagnesium chloride, adamantylmagnesium bromide, 3-cholestanylmagnesium chloride, 1-tetradecylmagnesium bromide, 3-methylbenzylmagnesium chloride, 2-methoxyphenylmagnesium bromide, 3-(2-dioxolanyl)-phenylmagnesium bromide, crotylmagnesium bromide, 4-hexadecylphenylmagnesium bromide, 11,11-dimethoxyundecylmagnesium bromide, 5-trimethylsilyloxypentylmagnesium iodide, 4-trifluoromethylphenylmagnesium bromide, 9,10-diphenyl-2-anthrylmagnesium chloride, vinylmagnesium chloride, and 2-thienylmagnesium iodide.

A preferred class of 1,2-amino alcohols produced by the process of this invention can be represented by the formula:

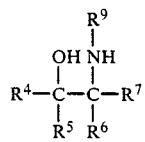

wherein
$R^4$, $R^5$, and $R^6$ are as defined above,
$R^7$ represents a member of the group consisting of hydrogen and $R^8$ wherein $R^8$ represents a member of the group consisting of alkyl groups, e.g., containing 1 to 30 carbon atoms, aralkyl groups, e.g., containing 7 to 30 carbon atoms, alkaryl groups, e.g., containing 7 to 30 carbon atoms, and aryl groups, e.g., containing 6 to 30 carbon atoms, said groups being optionally substituted with various groups which are inert to the reaction conditions of step (2), such as alkoxy aryloxy, alkaryloxy, aralkoxy, silyloxy, and halo, and $R^9$ represents a member of the group consisting of hydrogen and $R^{10}CH_2$ wherein a $R^{10}$ represents a member of the group consisting of alkyl groups, e.g., containing 1 to 20 carbon atoms, aralkyl groups, e.g., containing 1 to 12 carbon atoms, alkaryl groups, e.g., containing 1 to 12 carbon atoms, and aryl groups, e.g., containing 6 to 14 carbon atoms, said groups being optionally substituted with various groups which are inert to the reaction conditions of step (2), such as alkoxy, aryloxy, alkaryloxy, aralkoxy, silyloxy, and halo.

The reaction of the silylated cyanohydrin compound with the Grignard reagent can be accomplished by adding a solution of the silylated cyanohydrin compound to the Grignard reagent. It is preferred that the solution of silylated cyanohydrin compound be added dropwise to the Grignard reagent over a period of about one-half to one hour. The reaction, which is depicted by Equation (1) and is believed to result in the magnesium salt of the alpha-silyloxy imine is mildly exothermic-less so than the reaction wherein the Grignard reagent is prepared. Consequently, external cooling of the reaction mixture can usually be avoided.

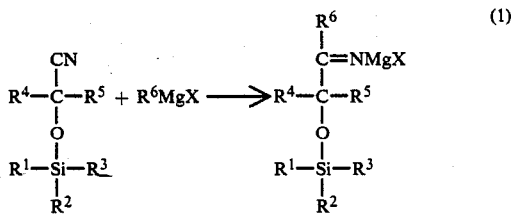

(1)

wherein $R^1$, $R^2$, $R^3$, $R^4$, $R^5$, and $R^6$ are as defined above.

Solvents that are appropriate to dissolve the silylated cyanohydrin reactant are the solvents which are suitable for use in the preparation of the Grignard reagent. After the addition of the solution of the silylated cyanohydrin compound has been completed, the reaction mixture can be refluxed to ensure that all the silylated cyanohydrin has reacted. Preferably, the reaction mixture is refluxed for an additional 1 to 2 hours or stirred at room temperature for longer periods of times, e.g. 12 to 16 hours.

Though stoichiometric amounts can be used, generally, an excess of up to 200 mole percent of the Grignard reagent, with a preferred excess of up to 100 mole percent, and a more preferred excess of 5 to 25 mole percent, can be employed. Use of substantial excesses of Grignard reagent, i.e. greater than 25 mole percent, has been discovered to result in diminished yields and much more complicated reaction product mixtures.

Various reducing agents are suitable for the second step of the process of this invention. The following classes of reducing agents are preferred:

(a) hydride reducing agents such as metal aluminum hydrides, e.g. lithium aluminum hydride and lithium trialkoxyaluminum hydride, metal borohydrides, e.g. lithium, sodium, potassium, calcium and zinc borohydrides, sodium cyanoborohydride, borane, borane complexes with amines, e.g. tert-butylamine, diethylaniline, dimethylamine, N-ethylmorpholine, 2,6-lutidine, morpholine, N-phenylmorpholine, poly(2-vinyl pyridine), pyridine, triethylamine, and trimethylamine, borane complexes with sulfides, e.g. methyl sulfide and 1,4-oxathiane, borane complexes with phosphines, e.g. tri-n-butylphosphine, borane complexes with phosphites, e.g. triphenylphosphite, a borane complex with tetrahydrofuran, other boron reducing agents, e.g. 9-borabicyclo[3.3.1]nonane, disiamylborane, thexylborane, -isopinocampheyl-9-borabicyclo[3.3.1]nonyl hydride, sodium bis(2-methoxyethoxy)aluminum hydride, sodium diethyldihydroaluminate, and diisobutylaluminum hydride;

(b) hydrogen in the presence of a metal catalyst such as finely dispersed palladium, platinum, or Raney nickel;

(c) dissolving metals such as lithium, magnesium, potassium or sodium dissolved in an alcohol such as methanol or ethanol; and (d) sodium dithionite.

A preferred reducing agent is sodium borohydride and the reduction step can be conveniently carried out by adding a solution of sodium borohydride in an alcohol such as methanol, ethanol, or propanol to the solution of the reaction product of Equation (1) at room temperature. However, the reduction may also be carried out at a lower temperature. It has been found that the temperature of the reduction influences the ratio of the diastereomers of the 1,2-amino alcohols. The diastereomeric ratio can be influenced by changing the reducing agent, for example by utilizing magnesium metal in methanol or zinc borohydride or lithium aluminum hydride instead of sodium borohydride as the reducing agent. It is often desirable to influence the diastereomeric ratio because, in the case of pharmaceuticals, one diastereomeric 1,2-amino alcohol may have very different physical and biological properties than the other diastereomer.

Additionally, further elaborated 1,2-amino alcohols can be prepared by adding an organolithium reagent, $R^8Li$, to the reaction product of Equation (1), wherein $R^8$ is as previously defined. Representative examples of organolithium reagents that are suitable for use in the preparation of the further elaborated 1,2-aminoalcohols include methyllithium, n-butyllithium, phenyllithium, vinyllithium, hexadecyllithium, 4,4-dimethyl-2-lithiomethyl-2-oxazoline, and 4-methoxyphenyllithium. In this instance, the process may be illustrated by Scheme 1:

Scheme 1

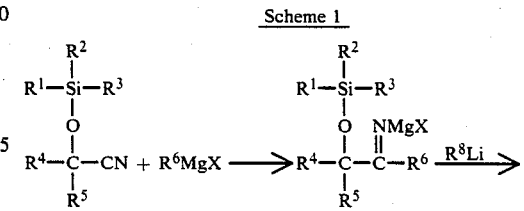

-continued
Scheme 1

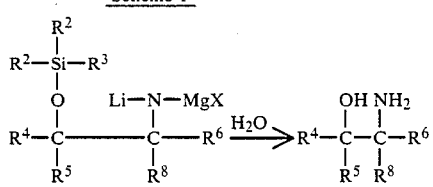

An amino alcohol with a substituent on nitrogen other than hydrogen where the substituent on nitrogen corresponds to a reduced carboxylic acid can also be prepared. This can be conveniently accomplished by adding a mixture of sodium borohydride and a carboxylic acid rather than sodium borohydride and an alcohol to the solution of the reaction intermediate from Equation (1). For example, if acetic acid is used, the N-ethyl amino alcohol is produced. It is well-known that many pharmaceutically important 1,2-amino alcohols have substituents other than hydrogen on nitrogen. In general, if a carboxylic acid having the formula $R^{10}CO_2H$ is utilized in this step, $R^9$ of formula III is $R^{10}CH_2$ wherein $R^{10}$ is as previously defined. Representative carboxylic acids of formula $R^{10}COOH$ which may be utilized include acetic acid, propionic acid, formic acid, butyric acid, pivalic acid, benzoic acid, trifluoroacetic acid, isobutyric acid, palmitic acid, monochloroacetic acid, stearic acid. If a carboxylic acid is not utilized in this step, then $R^9$ of formula III is hydrogen.

After either the reduction of intermediate from Equation (1) or the addition of an organolithium reagent to the intermediate from Scheme 1, hydrolysis to form the 1,2-amino alcohol can be effected by first adding an aqueous solution of an acid having a pKa of less than about 5 to the reaction mixture. Acids that can be used in this step of the process are hydrochloric acid, sulfuric acid, nitric acid, and phosphoric acid, with hydrochloric acid being preferred. The mixture is then stirred, preferably at room temperature for a period of about one hour.

Isolation and recovery of the 1,2-amino alcohol product can be accomplished in several ways, the following being expedient. The aqueous acidic layer is separated from the organic layer of Step (3), and the organic layer is extracted with several additional portions of an aqueous acid solution. By the extraction procedure, the basic 1,2-amino alcohol product is separated from any non-basic side products from the reaction. The aqueous acid solutions are combined with the original aqueous acidic layer, and then to this combination an aqueous solution of sodium hydroxide, potassium hydroxide, or ammonium hydroxide is added to raise the pH of the original aqueous layer to about 8 to 10. In some cases this will cause the 1,2-amino alcohol to precipitate immediately, and it can then be isolated by simple filtration. In other cases, the 1,2-amino alcohol product does not precipitate immediately, but it can be isolated by means of extraction with a suitable organic solvent. As one example, the aqueous alkaline layer can be extracted with several portions of chloroform and the chloroform extracts combined. The chloroform can be removed from the combined extracts by evaporation, leaving the 1,2-amino alcohol product, usually in a very pure form. Further purification can be effected by distillation or recrystallizaton of the 1,2-amino alcohol product. In addition, the 1,2-amino alcohol can be converted to a salt by treatment with an acid, for example, hydrobromic, hydrochloric, maleic, or tartaric acid.

The invention can be further illustrated by the following non-limiting examples.

EXAMPLE 1

STEP 1

To a stirred solution of phenyl magnesium bromide was added dropwise a solution of 5.15 g (25 mmol) of the O-trimethylsilylated cyanohydrin of benzaldehyde dissolved in 75 mL of anhydrous diethyl ether. When the addition was complete, the reaction mixture was stirred overnight at room temperature.

STEP 2

A solution of 0.95 g (25 mmol) of sodium borohydride in 25 mL of methanol containing a few drops of a 10% solution of sodium hydroxide in water was added dropwise. The mixture was stirred for 3 hours at room temperature.

STEP 3

Then 100 mL of a 10% solution of hydrochloric acid in water was added and the mixture stirred for 1 hour. Diethyl ether (100 mL) was added.

STEP 4

The layers were separated, and the organic layer was extracted three times with 75 mL portions of a 10% aqueous hydrochloric acid solution. All the aqueous washings were combined and the pH adjusted to a value between 8 and 10 by the addition of about 300 mL of concentrated ammonium hydroxide solution. The white precipitate which formed was collected by filtration and dried. The aqueous filtrate was extracted with three 100 mL portions of chloroform. The combined chloroform extracts were washed with 75 mL of brine, dried over potassium carbonate, filtered, and evaporated to leave a white solid which was combined with the solid from the filtration to give 5.2 g (98%) of 2-amino-1,2-diphenyl ethanol as a 16:1 mixture of erythro and threo diastereomers as determined by $^1$H-NMR.

The O-trimethylsilylcyanohydrin of benzaldehyde used in STEP 1 was prepared by the following method:

In a one liter, three-necked, round bottomed flask equipped with a mechanical stirrer, a reflux condenser fitted with a nitrogen-inlet tube, and a rubber septum were placed 97.5 grams (1.5 moles) of finely ground potassium cyanide (passed through a #30 sieve and dried at 115° C. at 0.5 torr for 24 hours), 100 mL of acetonitrile (dried over 4A molecular sieves), 81.4 grams (0.75 mole, 92.2 mL) of chlorotrimethylsilane, 53 grams (0.5 mole) of benzaldehyde and 0.5 gram (0.0004 mole) of zinc cyanide. The reaction was blanketed with dry nitrogen, stirring was begun, and the temperature raised to maintain gentle refluxing. After 21 hours, the reaction was complete, as evidenced by disappearance of benzaldehyde in the glpc analysis of a small sample taken from the reaction mixture. The reaction mixture was cooled and filtered with suction. The filter cake was washed twice with 50 mL of acetonitrile, and the combined filtrates were concentrated on a rotary evaporator. The residue was distilled at 93°–95° C. at 1.75 torr and weighed 84.0 grams (95% yield). The structure of the product was corroborated by spectral analyses.

Phenyl magnesium bromide used in STEP 1 was prepared by the following method:

Into a dry 500 ml, three-necked, round-bottomed flask equipped with a magnetic stirrer, argon inlet, addition funnel and condenser were placed 1.1 g (45 mg atom) of magnesium turnings and 10 mL of anhydrous diethyl ether. A solution of 5.5 g (35 mmol) of bromobenzene in 75 mL of anhydrous diethyl ether was added dropwise at such a rate that gentle refluxing of the solvent occurred. After the addition was complete, the solution was stirred for two hours.

EXAMPLES 2-6

The 1,2-amino alcohols listed in Table 1 and within the scope of formula III were obtained by the procedure described in Example 1.

TABLE 1

| Example | $R^4$ | $R^5$ | $R^6$ | $R^7$ | $R^9$ | Yield, % |
|---|---|---|---|---|---|---|
| 2 | $CH_3$ | $CH_3$ | $C_6H_5$ | H | H | 93 |
| 3 | $CH_3$ | $CH_3$ | $C_6H_{13}$ | H | H | 80 |
| 4 | $CH_3$ | $CH_3$ | c-$C_5H_9$ | H | H | 63 |
| 5 | —$(CH_2)_5$—* | | $CH_3$ | H | H | 88 |
| 6 | —$(CH_2)_5$—* | | $C_6H_5$ | H | H | 74 |

*—$(CH_2)_5$— along with the carbon atom to which it is bonded represents the cyclohexyl radical.

EXAMPLES 7-13

These examples indicate the influence of reducing agent and reduction temperature on the diastereomeric ratio of the 1,2-amino alcohols produced.

The 1,2-amino alcohols listed in Table 2 and within the scope of formula III were obtained by the procedure described in Example 1 except that the conditions of reduction were varied as indicated in Table 2.

methylmagnesium iodide. To prepare the reducing agent, 2.5 g (68 mmol) of sodium borohydride was added to 25 mL of acetic acid in a separate reaction vessel, while the temperature of the solution was maintained below 20° C. This solution was then added dropwise to the reaction intermediate from the silylated cyanohydrin and Grignard reagent, and the mixture stirred for 5 hours. The solvent was then evaporated, 100 mL of diethyl ether and 25 mL of a 10% aqueous hydrochloric acid solution added to the residue, and the extractive work-up outlined in Example 1 was followed to yield 2.1 g of a gold semi-solid which was a 4:1 mixture of erythro and threo diastereomers of the desired N-ethylated amino alcohol, as determined by $^1$H-NMR.

EXAMPLE 15

Preparation of 3-amino-2-methyl-3-phenyl-nonan-2-ol

By the procedure described in Example 1, 3.9 g (25 mmol) of the O-trimethylsilylated cyanohydrin of acetone were reacted with 27.5 mmol of n-hexylmagnesium bromide. To the reaction mixture was added 11.5 mL (27.5 mmol) of a solution of phenyllithium (2.4 molar in hexane-diethyl ether), and the mixture was stirred for 18 hours. Then 30 mL of a 10% aqueous hydrochloric acid solution were added and the extractive work-up of Example 1 was followed to yield 1.5 g of a white solid, mp. 64.5°–65.5° C.

Various modifications and alterations of this invention will become apparent to those skilled in the art without departing from the scope and spirit of this invention, and it should be understood that this invention is not to be unduly limited to the illustrative embodi-

TABLE 2

| Example | $R^4$ | $R^5$ | $R^6$ | $R^7$ | $R^9$ | Reducing Agent | Temperature °C. | Yield % | Diastereomeric Ratio,* Erythro:Threo |
|---|---|---|---|---|---|---|---|---|---|
| 7 | $C_6H_5$ | H | $C_6H_5$ | H | H | $LiAlH_4$ | 23 | 45 | 11.0 |
| 8 | $C_6H_5$ | H | $C_6H_5$ | H | H | $Mg/CH_3OH$ | 50 | 56 | 1.1 |
| 9 | 3,4-(CH$_3$O)$_2$C$_6$H$_3$ 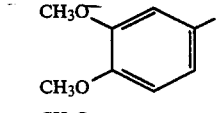 | H | $CH_3$ | H | H | $NaBH_4$ | 23 | 85 | 4.3 |
| 10 | 3,4-(CH$_3$O)$_2$C$_6$H$_3$ 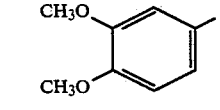 | H | $CH_3$ | H | H | $NaBH_4$ | 0 | 95 | 4.9 |
| 11 | 3,4-(CH$_3$O)$_2$C$_6$H$_3$ 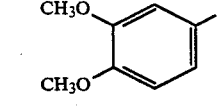 | H | $CH_3$ | H | H | $NaBH_4$ | −78 | 90 | 24 |
| 12 | 3,4-(CH$_3$O)$_2$C$_6$H$_3$ 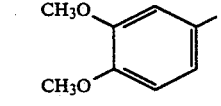 | H | $CH_3$ | H | H | $Zn(BH_4)_2$ | 23 | 96 | 7.3 |
| 13 | 3,4-(CH$_3$O)$_2$C$_6$H$_3$ 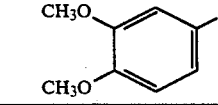 | H | $CH_3$ | H | H | $Zn(BH_4)_2$ | −78 | 74 | 13.3 |

*Ratio determined by $^1$H-NMR.

EXAMPLE 14

Preparation of 1-(3,4-dimethoxyphenyl)-2-ethylamino-propan-1-ol

By the procedure described in Example 1, 2.4 g (9.0 mmol) of the O-trimethylsilylated cyanohydrin of 3,4-dimethoxybenzaldehyde were reacted with 15 mmol of ments set forth herein.

What is claimed is:

1. Process for the preparation of 1,2-amino alcohol comprising the steps of (a) reacting a silylated cyanohydrin with a Grignard reagent to produce a magnesium salt of the alpha-silyloxy imine,
(b) treating the reaction product of step (a) with either a reducing agent or an organolithium compound,
(c) hydrolyzing the reaction product of step (b), and
(d) isolating the 1,2-amino alcohol.

2. The process of claim 1 wherein the silylated cyanohydrin is represented by the formula

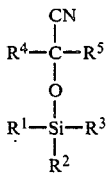

wherein
$R^1$, $R^2$, and $R^3$ can be the same or different and independently represent a member of the group consisting of hydrogen, alkyl groups, aralkyl groups, alkaryl groups, aryl groups, and alkoxy groups, and
$R^4$ and $R^5$ independently represent a member of the group consisting of hydrogen, alkyl groups, aralkyl groups, alkaryl groups, and aryl groups, or $R^4$ and $R^5$, along with the carbon atom to which they are bonded, together represent a cycloalkyl group, said alkyl, cycloalkyl, aralkyl, alkaryl and aryl groups of $R^4$ and $R^5$ being optionally substituted with various groups which are inert to the reaction conditions of step (a).

3. The process of claim 1 wherein the Grignard reagent is represented by the formula $R^6MgX$ wherein
$R^6$ represents a member of the group consisting of alkyl groups, aralkyl groups, alkaryl groups, and aryl groups, said groups being optionally substituted with various groups which are inert to the reaction conditions of step (a), and
X represents chloro, bromo or iodo, and wherein the magnesium salt of the alpha-silyloxy imine is represented by the formula

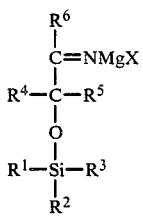

wherein
$R^1$, $R^2$, and $R^3$ can be the same or different and independently represent a member of the group consisting of hydrogen, alkyl groups, aralkyl groups, alkaryl groups, aryl groups, and alkoxy groups, and
$R^4$ and $R^5$ independently represent a member of the group consisting of hydrogen, alkyl groups, aralkyl groups, alkaryl groups, and aryl groups, or $R^4$ and $R^5$, along with the carbon atom to which they are bonded, together represent a cycloalkyl group, said alkyl, cycloalkyl, aralkyl, alkaryl and aryl groups of $R^4$ and $R^5$ being optionally substituted with the various groups which are inert to the reaction conditions of step (a).

4. The process of claim 1 wherein the 1,2-amino alcohol is represented by the formula:

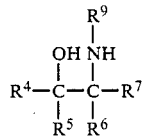

wherein
$R^4$ and $R^5$ independently represent a member of the group consisting of hydrogen, alkyl groups, aralkyl groups, alkaryl groups, and aryl groups, or $R^4$ and $R^5$, along with the carbon atom to which they are bonded, together represent a cycloalkyl group, said alkyl, aralkyl, and aryl groups of $R^4$ and $R^5$ being optionally substituted with various groups which are inert to the reaction conditions of step (a),
$R^6$ represents a member of the group consisting of alkyl groups, aralkyl groups, alkaryl groups, and aryl groups, said groups being optionally substituted with various groups which are inert to the reaction conditions of step (a),
$R^7$ represents a member of the group consisting of hydrogen and $R^8$ wherein $R^8$ represents a member of the group consisting of alkyl groups, aralkyl groups, alkaryl groups, and aryl groups, said groups being optionally substituted with various groups which are inert to the reaction conditions of step (b), and
$R^9$ represents a member of the group consisting of hydrogen and $R^{10}CH_2$ wherein $R^{10}$ represents a member of the group consisting of alkyl groups, aralkyl groups, alkaryl groups, and aryl groups, said groups being optionally substituted with various groups which are inert to the reaction conditions of step (b).

5. The process of claim 1 wherein the reducing agent is selected from the group consisting of hydrides, hydrogen in the presence of metal catalysts, metals dissolved in alcohol, and sodium dithionite.

6. The process of claim 5 wherein the reducing agent is sodium borohydride.

7. The process of claim 1 wherein the reducing step is conducted at a temperature below about 25° C. at 1 atm pressure.

8. The process of claim 6 wherein the reducing step is conducted at a temperature below about 25° C. at 1 atm pressure.

9. The process of claim 1 wherein the hydrolysis step is conducted with an acid having a pKa of 5 or lower.

10. The process of claim 9 wherein said acid is a mineral acid.

11. The process of claim 1 wherein $R^4$ is an alkyl group or an aryl group.

12. The process of claim 1 wherein $R^5$ is an alkyl group or an aryl group.

13. The process of claim 1 wherein $R^4$ and $R^5$ together are a cycloalkyl group.

14. The process of claim 1 wherein $R^6$ is an alkyl or an aryl group.

15. The process of claim 11 wherein $R^4$ is a substituted alkyl group or a substituted aryl group.

16. The process of claim 12 wherein $R^5$ is a substituted alkyl group or a substituted aryl group.

17. The process of claim 14 wherein $R^6$ is a substituted alkyl group or a substituted aryl group.

* * * * *